US00PP33250P2

(12) United States Plant Patent
Martinez et al.

(10) Patent No.: US PP33,250 P2
(45) Date of Patent: Jul. 13, 2021

(54) SEEDLESS TABLE GRAPE GRAPEVINE 'ITUMSIX'

(50) Latin Name: *Vitis vinifera*
Varietal Denomination: Itumsix

(71) Applicant: Investigacion y Tecnologia de Uva de Mesa S.L., Blanca (ES)

(72) Inventors: Manuel Tornel Martinez, La Alberca (ES); Juan Carreno Espin, Muricia (ES)

(73) Assignee: Investigacion y Tecnologia de Uva de Mesa S.L.

( * ) Notice: Subject to any disclaimer, the term of this patent is extended or adjusted under 35 U.S.C. 154(b) by 0 days.

(21) Appl. No.: 16/988,227

(22) Filed: Aug. 7, 2020

(51) Int. Cl.
*A01H 6/88* (2018.01)
*A01H 5/08* (2018.01)

(52) U.S. Cl.
USPC ..... Plt./205

(58) Field of Classification Search
USPC ..... Plt./207
See application file for complete search history.

(56) References Cited

PUBLICATIONS

PLUTO Plant Variety Database Jan. 23, 2021, p. 1.*
Workshop en Investigacion Agroalimentaria Cartagena May 12-13, 2014.*

* cited by examiner

*Primary Examiner* — Annette H Para
(74) *Attorney, Agent, or Firm* — Cassandra Bright

(57) ABSTRACT

A new and distinct variety of grapevine named 'Itumsix' is herein disclosed. 'Itumsix' abundantly forms medium yellow green seedless berries with an attractive narrow, circular ellipsoid berry shape, a neutral flavor and a very crunchy and firm berry texture. Being an early season variety, the fruit commonly is ready for harvesting from July to early September in Blanca, Murcia, Spain. 'Itumsix' displays good eating qualities as a table grape, the fruit meatiness and firmness render the fruit amenable for handling, shipping, and storage.

4 Drawing Sheets

Latin name of the genus and species: *Vitis vinifera.*
Variety denomination: 'ITUMSIX'.

BACKGROUND OF THE INVENTION

A breeding program was initiated during 2003 at a research nursery in Blanca, Murcia, Spain. During the development of this breeding program, a new variety of *Vitis vinifera* was created by deliberate cross breeding of two parent plants by emasculation of the pollen bearing organ of the female and introducing pollen from another male origin. The female parent of the new variety is 'ITUM 02-12-97', an unpatented proprietary selection. The male parent (i.e. the pollen parent) of the new variety is 'Princess', unpatented.

'Itumsix' was identified as a potentially interesting selection during 2009 at the same location in Murcia, Spain. After identifying the new variety as a potentially interesting selection, first propagation of 'Itumsix' by vegetative cuttings was undertaken during 2010, at the research nursery in Murcia, Spain. Controlled testing and propagation of the new variety continued, to assess stability of the unique characteristics of this variety. Subsequently, several generations have been reproduced and have shown that the unique features of this cultivar are stable and reproduced true to type. No publications have been issued on the plant breeding invention. Date of first sale was Nov. 22, 2019, occurring in Europe. This sale was made directly by the inventor or one who obtained the claimed invention directly or indirectly from the inventor. This sale and all public disclosures made between Nov. 22, 2019 and the filing of this application fall within the exception allowed under 102(b)(1).

SUMMARY OF THE INVENTION

The cultivar 'Itumsix' has not been observed under all possible environmental conditions. The phenotype may vary somewhat with variations in environment such as temperature, day length, and light intensity, without, however, any variance in genotype. The new variety 'Itumsix' is yellow green seedless table grape with medium production and a standard fertility index "1". In addition to the before mentioned characteristics, the following traits have been repeatedly observed and are determined to be the unique characteristics of 'Itumsix' These characteristics in combination distinguish 'Itumsix' as a new and distinct *Vitis* cultivar:

1. Individual fruit with medium yellow green skin coloration; formed in medium-to-large clusters.
2. An attractive narrow, circular ellipsoid berry shape and a crunchy and firm berry texture
3. A mid-season variety, commonly bears fruit for harvesting from July to early September in the region of Murcia, Spain.
4. Very firm berry texture.
5. Absence of seeds.
6. Resistance to cracking.
7. Fruit has been found to be suitable for handling and shipping.
8. Observed tolerance of water shortage.
9. Observed tolerance for temperatures up to 41° C.
10. Neutral flavor profile.

COMPARISON TO PARENT VARIETIES

TABLE 1

| Characteristic | 'Itumsix' | Parental A (fem) ITUM '02-12-97' |
|---|---|---|
| Berry skin color | Medium yellow-green | Red |
| Formation of seeds | Seedless | Rudimentary |

| Characteristic | 'Itumsix' | Parental B (masc.) 'Princess' |
|---|---|---|
| Berry Flavor: | Neutral | Muscat |
| Formation of seeds | seedless | Rudimentary |
| Berry shape: | Narrow circular ellipsoid | Ovoid |

COMMERCIAL COMPARISON

TABLE 2

| Characteristic | 'Itumsix' | 'Sheegene-4' (U.S. Plant Pat. No. 20,753) |
|---|---|---|
| Mature leaf: number of lobes | 3 | 5 |
| Formation of seeds | seedless | rudimentary |
| Ripening Time | Early | Late |

| Characteristic | 'Itumsix' | 'Sultanina' (unpatented) |
|---|---|---|
| Berry texture | Very firm | Moderately firm to soft |
| Mature leaf: depth of lateral sinuses | Very shallow | Moderately deep |

BRIEF DESCRIPTION OF THE PHOTOGRAPHS

The accompanying photographic illustration shows typical samples of vegetative growth of a 8 year old specimens of the new variety, in color as nearly true as it is reasonably possible to make in a color illustration of this character. Plants were grown in Murcia, Spain. Colors in the photograph may differ from the color values cited in the detailed botanical description below, which accurately describes the colors of the new Grapevine.

DETAILED BOTANICAL DESCRIPTION

Figure 1:
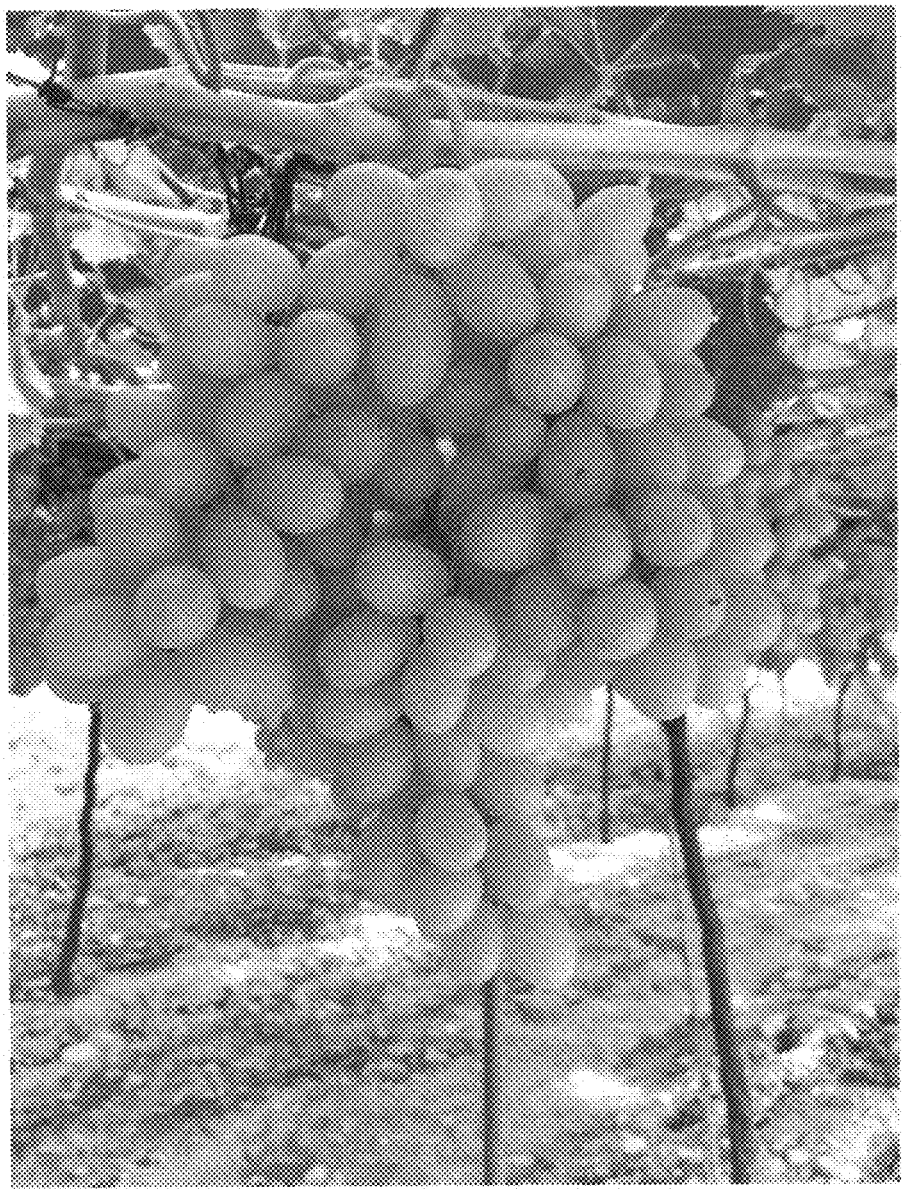
FIG. 1 illustrates a fruit cluster of 'Itumsix'.
Figure 2:
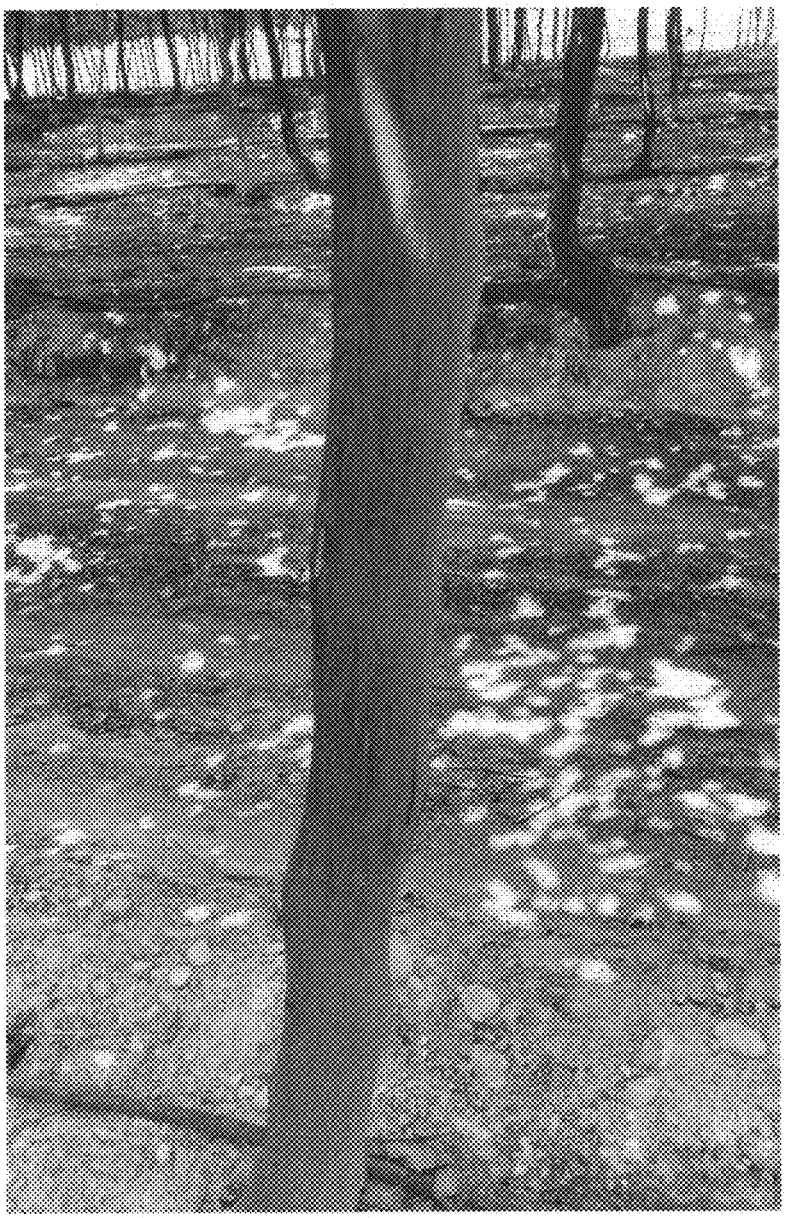
FIG. 2 shows a close up view of the trunk of 'Itumsix'.
Figure 3:
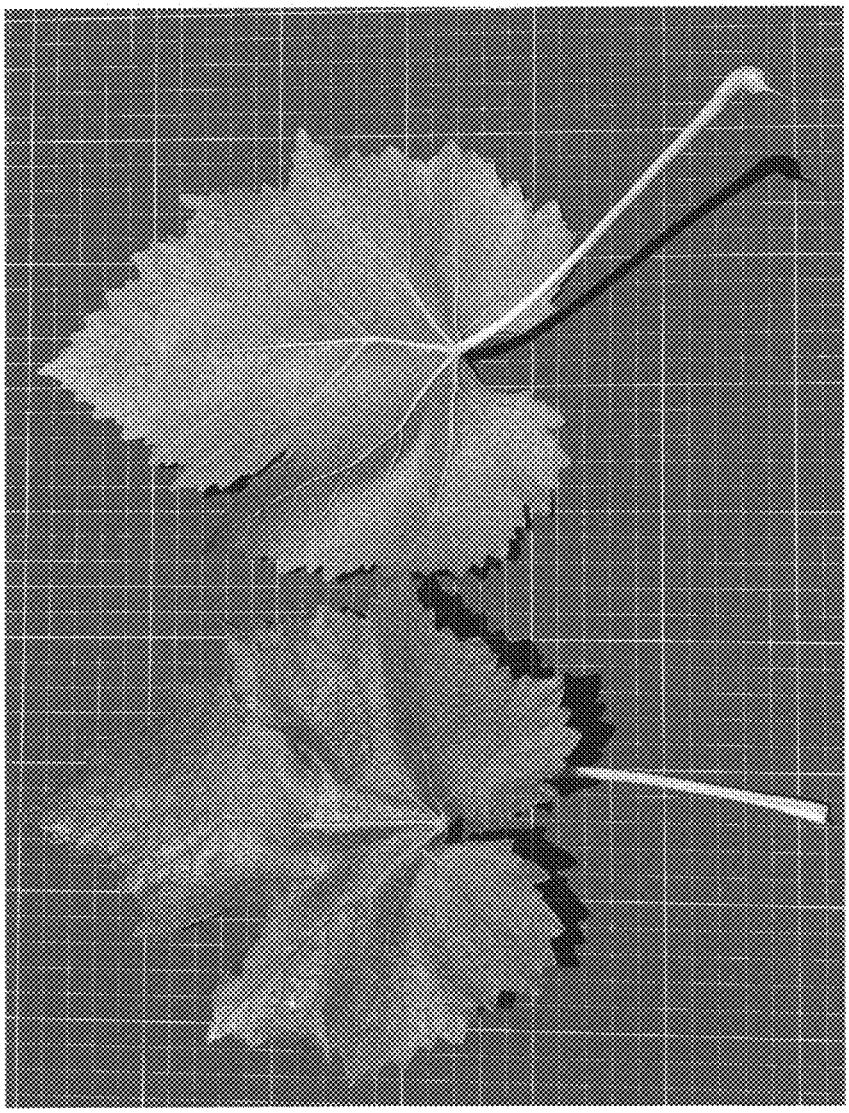
FIG.3 illustrates in close up perspective typical foliage of the new variety, both front and back of the leaf.
Figure 4:
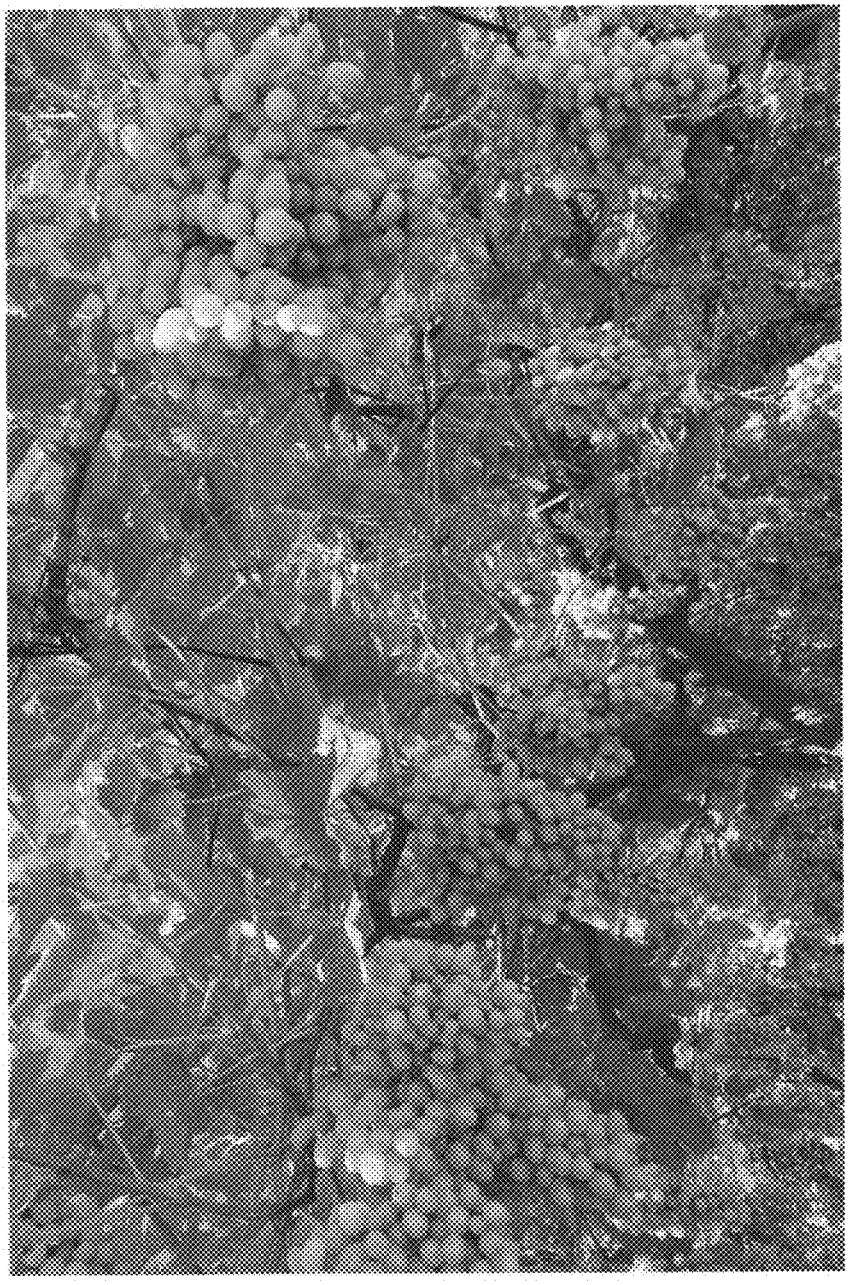
FIG. 4 illustrates the plant canopy of 'Itumsix', including fruits, branches and foliage.

In the following description, color references are made to The Royal Horticultural Society Colour Chart 2015 except where general terms of ordinary dictionary significance are used. Some descriptors, when useful have been incorporated from *UPOV Grape Descriptor Guidelines*. The description is based on the observation of plants growing on '1103 Paulsen' rootstock in clay stony soil conditions in the fields near Blanca, Murcia, Spain. The age of plant described is of 8 years, with an average height of 200 cm, a high canopy density, a 300 cm plant spread, a one-year growth rate to reach two meters high and 20 to 30 days to initiate roots at approximately 20° C. At observation location temperature ranged between 15° C. to 35° C. during the day, and between 5° C. to 20° C. during the night.

Botanical classification: *Vitis vinifera* 'Itumsix'.

CANES

Characteristics of mature canes:

*Diameter.*—1.3 cm to 1.5 cm.
*Length.*—55 cm to 70 cm.
*Color.*—Near RHS Greyed-Orange 164C.
*Cross section shape.*—Circle.
*Strength.*—Medium.
*Texture.*—Non-pubescent, rough, slightly scaly.

Lenticels:

*Diameter.*—<0.5 mm.
*Density.*—Few to-moderate.
*Color.*—Near RHS Greyed-Orange 164C.

Internode:

*Length.*—7-11 cm; midpoint 9 cm.
*Pigmentation at internode, dorsal.*—Near RHS Greyed-Orange 164C.
*Pigmentation at internode, ventral.*—Near RHS Greyed-Orange 164C.

Tendril:

*Pattern on show.*—0,0,0,0,0,1,0.
*Tendrils forked.*—Yes.
*Tendril texture.*—Firm.
*Tendril length.*—9 cm.

Bud:

*Width.*—0.8 cm.
*Bud length.*—0.3 cm.
*Bud shape.*—Triangular.
*Bud color.*—Near RHS Greyed-Yellow 161D and 162D both colors present individually.

Young shoot:

*Openness of tip.*—Open.
*Anthocyanin not present in shoot pigmentation.*
*Texture.*—Smooth.
*Diameter.*—0.8 to 1.1 cm.
*Longitudinal length.*—1.0 to 4.0 m; midpoint 2.0 m.
*Color.*—Near RHS Greyed-Orange 164D, streaked 165D.
*Cross section circular.*
*Strength.*—Low to medium.
*Attitude.*—Horizontal.
*Bark texture.*—Shaggy.
*Bark color.*—Near RHS Greyed-Red 178A streaked 180A.

FOLIAGE

Leaf:

*Arrangement.*—Alternate.
*Quantity.*—Approximately 15 per cane.
*Average length.*—22 cm.
*Average width.*—18 cm.
*Overall shape of blade.*—Broad ovate.
*Apex.*—Acute.
*Base.*—Rounded.
*Margin.*—3 lobed, dentate.
*Texture of top surface.*—Smooth.

*Texture of bottom surface*.—Smooth.
*Pubescence*.—None.
*Aspect*.—Slightly undulate.

Sinuses:
*Shape of petiolar sinus*.—High widened.
*Shape of base petiolar sinus*.—High widened.
*Depth of petiolar sinus*.—5 cm.
*Width of petiolar sinus*.—2.6 cm.
*Shape of upper sinuses*.—High widened.

Color:
*Immature foliage upper side*.—Near RHS Yellow-Green 154D streaked 150D.
*Immature foliage under side*.—Near RHS Yellow-Green 154D streaked 150D.
*Mature foliage upper side*.—Near RHS Green 137A.
*Mature foliage under side*.—Near RHS Yellow-Green 144A.

Venation:
*Type*.—Pinnate.
*Venation color upper side*.—Near RHS Yellow-Green 154C.
*Venation color under side*.—Near RHS Yellow-Green 154C.

Petiole:
*Length*.—15 cm.
*Diameter*.—0.5 cm.
*Color*.—Near RHS Yellow-Green 144A with no anthocyanin presence.
*Texture*.—Glabrous.

FLOWER

Flowering period begins around May 9 to 16 in Murcia, Spain.

Inflorescence when in bud:
*Length*.—11 cm.
*Diameter*.—5 cm.
*Bud color*.—Near RHS Green 140B.
*Bud shape*.—Conical.
*Bud size*.—About 1 to 2 mm by 1 to 2 mm.

Individual flower:
*Main time of flowering*.—7 days.
*Size of entire flower (to end of stamens)*.—0.6 cm.
*Calyx shape*.—Funnel.
*Calyx size*.—1.3 cm.
*Calyx color*.—Near RHS Green 140A.
*Calyx apex*.—Rounded.
*Calyx base*.—Rounded.
*Calyx texture*.—Glabrous all surfaces.
*Diameter*.—15 mm.
*Quantity per flowering stem*.—5.
*Days lasting on plant*.—7 days.

Petals:
*Quantity*.—5.
*Arrangement*.—Symmetrical rotate.
*Length*.—0.19 cm.
*Width*.—<0.1 cm.
*Shape*.—Obovate.
*Apex*.—Ovate.
*Base*.—Ovate.
*Texture, upper and lower surfaces soft*.
*Color*.—At opening upper surface: Near RHS Green 140B. At opening lower surface: Near RHS Green 140B. Fully opened upper Surface: Near RHS Green 140B.

Peduncles:
*Fruit peduncle length*.—45 mm.
*Fruit peduncle width*.—4 mm.
*Angle*.—About 65° to the lateral branch.
*Fruit peduncle strength*.—Medium.
*Fruit peduncle texture*.—Softly pubescent.
*Color*.—Near RHS Green 142D.

Pedicels:
*Length*.—0.8 cm.
*Diameter*.—0.05 cm.
*Angle*.—About 70° to center of flower cluster.
*Strength*.—Very strong.
*Texture*.—Softly pubescent.
*Color*.—Near RHS Green 141C.

Fragrance: Absent.

REPRODUCTIVE ORGANS

Number of stamens.—5.

Anthers:
*Shape*.—Oblong.
*Length*.—Approximately 0.1 cm.
*Color*.—Near Yellow 9C.

Pollen:
*Color*.—Near Yellow 8A.

Quantity: Abundant.

Pistil quantity: 1.
*Length*.—0.3 cm.

Style:
*Length*.—<0.1 cm.
*Color*.—Near RHS Green 143B.

Stigma:
*Shape*.—Round.
*Color*.—Near RHS Yellow-Green 144D.

Ovary color: Near RHS Yellow-Green 144D.

FRUIT

Cluster:
*Average length*.—26 cm.
*Average diameter*.—21 cm.
*Average weigh*.—650 grams.
*Fertility index*.—Number of clusters per sprouted buds 1.

Fruit:
*Average length*.—2.9 cm.
*Average diameter*.—2.2 cm.
*Shape*.—Narrow circular ellipsoid.
*Cross-section*.—Circular.
*Color of berry skin*.—Near RHS Yellow-Green 154D.
*Color of berry flesh*.—Translucent, near White 155B.
*Brix at harvest*.—18.
*Ease of detachment from pedicle*.—Difficult, well hooked and difficult detachment.
*Thickness of skin*.—Thin.
*Firmness of flesh*.—Very crunchy and moderately firm.
*Particular flavor*.—Neutral.
*Formation of seeds*.—None. Seeds are absent in this variety.

OTHER CHARACTERISTICS

Disease and pest resistance: Not observed to be susceptible nor resistant to normal diseases and pests of *Vitis vinifera*.

Temperature tolerance: Observed growing between 6° C. to 41° C.

Temperature tolerance: Observed to tolerate water shortages during the dry Summer months of Murcia, Spain without detriment.

What is claimed is:

1. A new and distinct cultivar of *Vitis* grapevine named 'ITUMSIX' as herein illustrated and described.

* * * * *